(12) United States Patent
McCutchen et al.

(10) Patent No.: US 9,851,145 B2
(45) Date of Patent: Dec. 26, 2017

(54) RADIAL COUNTERFLOW REACTOR WITH APPLIED RADIANT ENERGY

(71) Applicant: McCutchen Co., Portland, OR (US)

(72) Inventors: David J. McCutchen, Portland, OR (US); Wilmot H. McCutchen, Orinda, CA (US)

(73) Assignee: MCCUTCHEN CO., Portland, OR (US)

( * ) Notice: Subject to any disclaimer, the term of this patent is extended or adjusted under 35 U.S.C. 154(b) by 407 days.

(21) Appl. No.: 14/333,276

(22) Filed: Jul. 16, 2014

(65) Prior Publication Data

US 2014/0325866 A1    Nov. 6, 2014

Related U.S. Application Data

(62) Division of application No. 13/360,564, filed on Jan. 27, 2012, now abandoned.
(Continued)

(51) Int. Cl.
*C12M 1/02* (2006.01)
*F26B 3/28* (2006.01)
(Continued)

(52) U.S. Cl.
CPC .............. *F26B 3/283* (2013.01); *A01K 61/59* (2017.01); *C12M 21/02* (2013.01); *C12M 27/02* (2013.01);
(Continued)

(58) Field of Classification Search
CPC ..................................................... C12M 21/02
See application file for complete search history.

(56) References Cited

U.S. PATENT DOCUMENTS

| 2,867,945 A | 1/1959 | Gotaas |
| 3,491,023 A | 1/1970 | McCormick |

(Continued)

FOREIGN PATENT DOCUMENTS

| GB | 2354462 | 3/2001 |
| WO | 2009142765 | 11/2009 |

OTHER PUBLICATIONS

"All Biochar is Not Created Equally"; http://www.biocharsolutions.com/technology.html; printed on Feb. 13, 2012.
(Continued)

*Primary Examiner* — William H Beisner
(74) *Attorney, Agent, or Firm* — Marger Johnson

(57) ABSTRACT

An improvement is described for the processing of biological material in a continuous stream by the application of radiant energy taken from the wavelengths from infrared to ultraviolet, and its absorption by a feedstock in a workspace of featuring controlled turbulence created by one or more counter-rotating disk impellers. The absorbed energy and the controlled turbulence patterns create a continuous process of productive change in a feed into the reactor, with separated light and heavy product output streams flowing both inward and outward from the axis in radial counterflow. The basic mechanism of processing can be applied to a wide range of feedstocks, from the promotion of the growth of algae to make biofuel or other forms of aquaculture, to a use in the controlled combustion of organic material to make biochar.

15 Claims, 5 Drawing Sheets

Related U.S. Application Data

(60) Provisional application No. 61/437,277, filed on Jan. 28, 2011.

(51) Int. Cl.

| | | |
|---|---|---|
| *C12M 1/00* | (2006.01) | |
| *C12M 1/06* | (2006.01) | |
| *C12M 3/04* | (2006.01) | |
| *C12N 1/06* | (2006.01) | |
| *C12N 1/12* | (2006.01) | |
| *C12N 13/00* | (2006.01) | |
| *C12P 7/64* | (2006.01) | |
| *A01K 61/59* | (2017.01) | |

(52) U.S. Cl.
CPC ............ *C12M 27/10* (2013.01); *C12M 31/10* (2013.01); *C12M 31/12* (2013.01); *C2N 1/066* (2013.01); *C12N 1/12* (2013.01); *C12N 13/00* (2013.01); *C12P 7/64* (2013.01); *Y10T 137/206* (2015.04)

(56) References Cited

U.S. PATENT DOCUMENTS

| | | | |
|---|---|---|---|
| 3,959,923 | A | 6/1976 | Selke |
| 4,324,068 | A | 4/1982 | Anthony |
| 4,341,038 | A | 7/1982 | Bloch et al. |
| 4,680,314 | A | 7/1987 | Nonomura |
| 6,037,170 | A | 3/2000 | Sekine |
| 6,350,890 | B1 | 2/2002 | Kiy et al. |
| 6,495,133 | B1 | 12/2002 | Xue |
| 7,163,637 | B2 | 1/2007 | Vannahme et al. |
| 7,757,866 | B2 | 7/2010 | McCutchen |
| 7,794,969 | B1 | 9/2010 | Reppas et al. |
| 7,851,211 | B2 | 12/2010 | Lu |
| 7,901,485 | B2 | 3/2011 | McCutchen |
| 2004/0048364 | A1 | 3/2004 | Trosch |
| 2005/0133464 | A1 | 6/2005 | Vannahme et al. |
| 2006/0011563 | A1 | 1/2006 | Meikrantz |
| 2007/0048848 | A1 | 3/2007 | Sears |
| 2007/0048859 | A1 | 3/2007 | Sears |
| 2007/0155006 | A1 | 7/2007 | Levin |
| 2007/0231886 | A1 | 10/2007 | Kahlert et al. |
| 2008/0086969 | A1 | 4/2008 | Taylor |
| 2009/0045150 | A1 | 2/2009 | McCutchen |
| 2009/0056201 | A1 | 3/2009 | Morgan |
| 2009/0068727 | A1 | 3/2009 | Karr |
| 2009/0113790 | A1 | 5/2009 | Erd |
| 2009/0155864 | A1 | 6/2009 | Bauer et al. |
| 2009/0159523 | A1 | 6/2009 | McCutchen |
| 2009/0241545 | A1 | 10/2009 | McCutchen |
| 2009/0246863 | A1 | 10/2009 | Lin |
| 2009/0317901 | A1 | 12/2009 | Vance |
| 2010/0005711 | A1 | 1/2010 | McNeff |
| 2010/0034050 | A1 | 2/2010 | Erb et al. |
| 2010/0093046 | A1 | 4/2010 | Remmereit et al. |
| 2010/0093074 | A1 | 4/2010 | Tooley |
| 2010/0162620 | A1 | 7/2010 | McCaffrey et al. |
| 2010/0178231 | A1 | 7/2010 | Turney et al. |
| 2010/0190241 | A1 | 7/2010 | Jaggi |
| 2010/0227388 | A1 | 9/2010 | Shvabsky et al. |
| 2010/0255569 | A1 | 10/2010 | Camarate de Albuquerque Maranhao |
| 2010/0273252 | A1 | 10/2010 | Lin |
| 2010/0330615 | A1 | 12/2010 | Neto |
| 2012/0036767 | A1* | 2/2012 | Larach .................. C12M 21/02 44/388 |

OTHER PUBLICATIONS

Chen, C. et al., Cultivation, photobioreactor design and harvesting of microalgae for biodiesel production: A critical review; Bioresource Technology 102 (2011) 71-81.

"Biochar Pathways for Different Environments"; International Biochar Initiative, Aug. 26, 2009, pp. 1-2.

Mata, T. et al., Microalgae for biodiesel production and other applications: A review; Renewable and Sustainable Energy Reviews 14 (2010) 217-232.

Park, W. et al., Determination of Pyrolysis Temperature for Charring Materials; National Institute of Standards and Technology, U.S. Dept. of Commerce, NIST GCR-07-913, Dec. 2007.

Sheehan, J. et al., A Look Back at the U.S. Department of Energy's Aquatic Species Program—Biodiesel from Algae; National Renewable Energy Laboratory, NREL/TP-580-24190, Jul. 1998.

Shelef, G. et al., "Microalgae Harvesting and Processing" A Literature Review; U.S. Department of Energy, Technion Research and Development Foundation Ltd.; SERI/STR-231-2396, Aug. 1984.

Ugwu, C. U. et al., "Photobioreactors for mass cultivation of algae"; Bioresource Technology 99 (2008) 4021-4028.

Zellwerk GmbH, "Cells Working for You"; retrieved at http://www.glenmills.com/index-z_rp.shtml; printed on Dec. 29, 2010.

"Algaewheel Brochure", retrieved at http://www.algaewheel.com (2012).

International Search Report dated May 16, 2012 corresponding to International Application No. PCT/US2012/023021.

* cited by examiner

RADIAL COUNTERFLOW REACTOR WITH APPLIED RADIANT ENERGY

APPLICATION HISTORY

This application is a divisional of co-pending U.S. patent application Ser. No. 13/360,564, filed Jan. 27, 2012, which claims the benefit of U.S. Provisional Patent Application No. 61/437,277 filed Jan. 28, 2011.

FIELD

The present disclosure is related to drying and gas or vapor contact with solids, by continuous processing with centrifugal force and heating; cleaning and liquid contact with solids with means for collecting escaping material; classifying, separating and assorting solids, with heat treatment; classifying, separating and assorting solids with fluid suspension with grading deposition of gaseous feed with fluidically induced, unidirectional swirling; or classifying, separating and assorting solids, with a liquid feed grading deposition including rotational hydrodynamic extraction; and pumps where one fluid is pumped by contact or entrainment with another within a rotary impeller, or by a jet.

BACKGROUND

The separation of the products of a reaction taking place within a feedstock is currently done in several ways. Examples include batch processing, gravity separation, and centrifugal separation. A new approach is a radial counterflow reactor, which uses a feedstock in a workspace with controlled turbulence patterns created by the rotation of one or more disk impellers, and is described in several disclosures by the present applicants.

There are currently a variety of vessels for the growth or other processing of biological material. The current approaches do not allow for the efficient application of energy throughout the material within the vessel, while simultaneously stripping out exceptionally beneficial or harmful components within the vessel in a continuous process which lends itself to high volume.

Two examples will be used here to illustrate this. The first is the promotion of algae growth for the production of biofuels from $CO_2$. Typically the algae is placed with sterilized water and nutrients in clear vessels such as tubes to allow sunlight to shine in, and $CO_2$ is bubbled up in the tubes to mix with the algae. There is inefficiency in the application of the sunlight energy to the tube, where much of the algae in the interior of the column are shielded from the sun while that on the exterior may get too much. A need exists for improved access of light for photosynthesis to algae in a bioreactor or in a pond.

The distribution of the $CO_2$ in the tube also tends to be uneven because there is not enough mixing. When the algae has had time to create oils and other hydrocarbons, which here will be generally called lipids, then the algae has to be extracted, dried, and processed to remove the lipids. This is a wasteful and energy intensive extra step, and because this is a batch process, there is not a continuous stream that would lend itself to high volume.

It would be preferable to have a continuous lipid production process that did not depend on killing the algae. A goal of research has been to engineer a "lipid trigger" in the algae to make it extrude lipids, instead of storing them internally, and to do so continuously, instead of only producing them intermittently during periods when there is no cell division. But if a live algae colony were able to be continuously producing lipids in this way, there is no efficient way to extract the lipids to keep them from contaminating the algae environment. There is also no way to, at the same time, continuously separate the dead algae from the live ones, to keep the most productive members flourishing. Also, there is a need to strip out the oxygen produced by the algae to favor the forward photosynthesis reaction for enhancing algae growth.

Where algae is in a pond, oxygen is produced by photosynthesis and released to the atmosphere, but dissolved oxygen in the water is consumed by the decay of dead algae, and the depletion of oxygen in the water leads to dead zones where fish cannot live.

In shrimp and fish aquaculture, oxygen is desired, instead of carbon dioxide, but the same need exists for continuous stripping of waste gases and circulation of water to extract feces and other waste material.

To use another example, the combustion of material to create biochar is typically done in furnaces in a batch process. There is a need for continuous mixing that ensures that heat energy will be evenly applied throughout the feedstock, and for an efficient mechanism for continuously stripping out volatile gases or liquids to aid the forward reaction.

The applicants have described a variety of variations on the design of a radial counterflow reactor comprising one or more rotating disk impellers, which has many benefits in establishing a radial counterflow pattern with lighter elements continuously migrating toward the axis, and heavier elements toward the periphery. This radial counterflow reactor idea has been described through its application to the continuous processing of gases, liquids and sludge.

SUMMARY

A radial counterflow reactor is described featuring radiant energy, from among the wavelengths from infrared to ultraviolet, applied to the workspace. The reactor typically comprises two approximately parallel counter-rotating disk impellers, defining a turbulent workspace between them. The workspace can also be defined by a single impeller approximately parallel to a static casing. The disk impellers are conductive to the radiant energy, allowing at least some portion of the radiant energy to pass through them into the workspace to transform the feed. The radiant energy can come from emitting elements which are outside of the impellers and the workspace, or the radiant energy can come from elements embedded in the impellers.

One example design is a photobioreactor with two counter-rotating disk impellers, defining a turbulent workspace between them. The disk impellers are transparent to radiant energy, to allow an applied radiant energy, from infrared to ultraviolet, to be transmitted through them into the workspace to transform the feed. This type of photobioreactor reactor is especially useful for the growth and processing of biological and organic material, including in aquaculture.

For example, algae can be grown between transparent disk impellers in an axenic closed photobioreactor system, with improved means for extraction of products such as lipids for oil production. The impellers can be oppositely rotating solid disks, or moving liquid disk layers created by an array of jets. The algae feedstock, together with water, $CO_2$ and nutrients, is fed into the workspace and slowly sheared by the impellers, creating a fractal network of branching vortices where controlled turbulence and centrifugal force spins heavier components toward the periphery of the vortices and toward the periphery of the disks. At the same time, suction applied to the axial port in the upper disk impeller by a suction pump draws the lighter products such as lipids inward in a sink flow through the cores of the vortices, to be exhausted out of the axial port. The transparent disk impellers can be solid or liquid. If moving liquid disk layers form the impellers, they can contain dissolved nutrients or gases to be supplied by diffusion to the workspace, and they can also carry away wastes through drains in the impeller layers. In addition, the liquid impeller layers can supply hot or cool water as needed. Dead algae sink and are swept to the periphery of the photobioreactor where they are extracted as a sludge. Continuous gentle churning of the algae in this way exposes more of them to the light and extracts the waste products.

In an embodiment for shrimp farming, algae and shrimp may coexist in the photobioreactor such that the shrimp eat the algae. Dead shrimp and feces are spun out by the disk impellers while live shrimp thrive among the live algae being nourished at the center. Methane and other waste gases are stripped out continuously and oxygen is introduced along with the recycled water.

In an embodiment for fish farming, feces and dead fish are spun to the periphery of the photobioreactor where they can be easily collected at a wall, while the water is extracted, clarified, degassed, and aerated prior to being reintroduced to the tank.

In another example design, biological and organic material is processed by radiant energy coming out of the solid impellers in a biochar reactor where wood or other organic waste is pyrolyzed by heat applied through heated impellers, with biochar accumulating at the periphery, and bio-oil and gases exhausted out of the axis.

DRAWING REFERENCE NUMERALS

Figure 1:
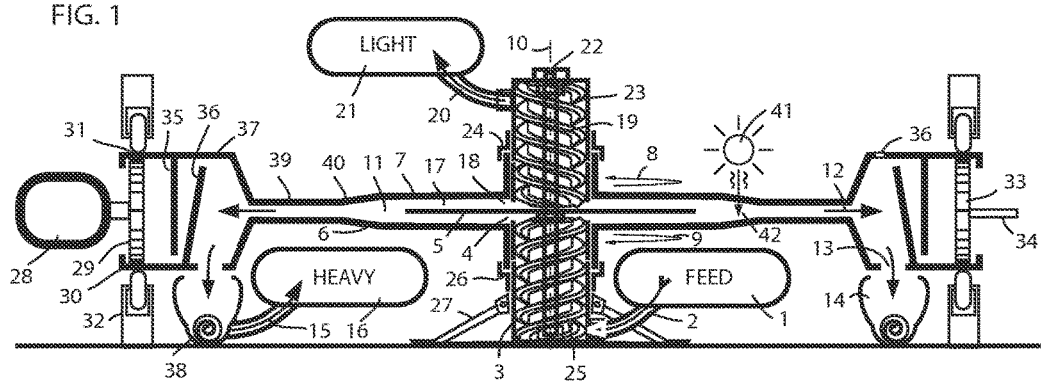
FIG. 1 shows a cross section of a radial counterflow reactor utilizing absorbed energy applied into a feedstock, showing the basic components, as well as the flow of a feedstock and energy into it, and the flow of byproducts out.

1—feed source
2—feed transfer
3—axial feed conduit
4—axial feed port
5—baffle
6—bottom disk impeller
7—top disk impeller
8—rotation of top disk impeller
9—rotation of bottom disk impeller
10—axis of rotation
11—workspace
12—periphery of the workspace
13—heavy products exhaust port
14—heavy products collection
15—heavy products transfer
16—heavy products storage
17—sink flow
18—axial exhaust port
19—axial suction pump
20—lighter products transfer
21—lighter products receptacle
22—axial support shaft
23—upper exhaust conduit
24—upper disk bearing and seal
25—lower intake conduit
26—lower disk bearing and seal
27—base support
28—prime mover
30—lower drive track
31—upper drive track
32—support wheel
33—sleeper wheel
34—sleeper wheel support
35—drive shield wall
36—output deflector wall
37—output vent
38—heavy product screw conveyor
39—pinch section
40—pinch opening
41—radiant energy source
42—absorption into feed
45—axial feed pump
46—feed flow
47—sink flow 48—heavy products flow
50—vortex in shear layer
51—vane on lower disk
52—vane on baffle
53—vane on upper disk impeller
54—crossflow filter inset into bottom disk impeller
55—liquid flow through crossflow filter
56—rugose ridges on bottom disk impeller
56a—gas vent on top disk impeller
57—rugose ridges on top disk impeller
60—boundary layer
61—direction of flow of boundary layer
62—flow from boundary layer to shear layer
63—shear layer
64—outer part of vortex
65—direction of flow of outer vortex
66—movement from shear layer to boundary layer
67—inner part of vortex
68—direction of flow of inner vortex
69—inward sink flow
70—vortex with counterclockwise rotation
71—vortex with counterclockwise rotation
72—centrifugal separation
73—bottom impeller
74—first vane
75—second vane
76—third vane
77—fourth vane
78—edge of baffle
79—conical apex of screw feed conveyor
80—vane crossing intersection
81—corresponding inverted vane on top disk impeller
82—first intersection axis
83—second intersection axis
84—third intersection axis
85—fourth intersection axis
86—fifth intersection axis
87—sixth intersection axis
88—seventh intersection axis
89—eighth intersection axis
90—rugose ridge on bottom disk impeller
91—example of corresponding inverted rugose ridge on top disk impeller
92—gas vent
93—drive shield wall brace
96—straight vane on bottom impeller
97—straight vane on top impeller
98—heavy products flow
99—light products sink flow
100—vortex network
101—main supply pipe
102—branch supply pipe
103—liquid jet nozzle
104—area of jet
105—direction of flow
106—drain inlet
107—drain pipe
108—central drain
109—central supply pipe
110—axial exhaust
111—support frame
112—support float
113—peripheral wall
114—upper liquid impeller
115—lower liquid impeller
116—turbulence flow
117—nutrients
118—waste products in liquid impeller
119—supply inlet
120—drain outlet

DETAILED DESCRIPTION

Three examples will be given of a radial counterflow reactor with radiant energy applied to the feed. Each comprises a closed vessel with one or more feed stock input ports, one or more output ports for lighter products, and one or more output ports for heavier products, plus a source of radiant energy, in wavelengths selected from infrared to ultraviolet, to be to be absorbed by the feedstock. The first example will describe a photobioreactor with solid impellers. The second example describes a more simplified photobioreactor with liquid impellers. Both of these examples use radiant energy transmitted through transparent impellers. The third example is a biochar processor which also uses solid impellers, which are heated, either by the application of external heat or internal heating elements.

Algae Processor

This reactor will first be described in an exemplary configuration as a photobioreactor for growing lipid-producing algae. It will be appreciated by the skilled practitioner that this example is not meant to restrict the possible applications of this description to the solution of other types of problems. Similarly, the design disclosed here is exemplary, and is not meant to preclude any modified design to suit a particular purpose.

A feed source 1 comprises storage for a transportable feed, such as algae, combined with water, $CO_2$, and nutrients. A feed transfer 2 brings the feed into the photobioreactor, by means such as pumps, conveyors or a gravity feed, into an axial feed conduit 3, leading to an axial feed port 4, where the feed enters the photobioreactor in a space underneath a baffle 5, which is located between a bottom disk impeller 6 and top disk impeller 7. These two disk impellers, which act as centrifugal pumps, rotate in opposite directions, such as those shown at 8 and 9, about an axis of rotation 10. A workspace 11 is defined in the space between the disk impellers. The workspace has boundary layers along the surfaces of the impellers, and a shear zone between the boundary layers, where amplified centrifugal force in organized vortex turbulence creates separation between the heavy and lighter products.

After the algae is introduced into the photobioreactor, it is expected to multiply and grow there within it, and the primary feed from then on will be water along with $CO_2$ and nutrients to promote proper growth.

The heavier products, such as an algae sludge, move toward the periphery of the workspace 12 where they are extruded, falling through a heavy products exhaust port 13 to be collected, in this case into an annular heavy products collection trough 14, where the heavy products transfer means 15 convey the heavy products to the heavy products storage 16. Meanwhile, while the heavy products migrate outward, an inward sink flow 17 is set up above the baffle, leading inward to an axial exhaust port 18. The sink flow is forced by an axial suction pump 19, in this case a screw conveyor. This pump can also be a mechanical pump or any other kind of appropriate pump to draw out the light products axially so a lighter products transfer 20 can convey them to a lighter products receptacle 21. These lighter products include anything with a lower specific gravity than the heavier products. For example, the lighter products can include lipids extruded by the algae and oils as well as gases including oxygen produced by photosynthesis.

The disks and the conveyor pumps in this design are supported by an axial support shaft 22, which extends downward through the upper exhaust conduit casing 23. This casing has the support for the upper disk bearing and seal 24, which preferably contains a combination thrust bearing and rotary seal. A similar disk bearing and seal is in the casing for the lower disk. If the disk bearing and seal 24 is made to be movable up and down, such as by a telescoping upper exhaust conduit casing 23 and/or a similar one for the bottom disk impeller, then the separation between the top and bottom disk impellers 7 and 6 can be changed if needed. For instance, in the example of algae, a relatively wide separation could be used for an algae growth process, and a narrower one could be used to concentrate and dewater a resulting algae sludge. The axial support shaft 22 preferably also extends down through the axial feed conduit 3, which has an axial feed pump 25, in this case a screw conveyor, and lower disk bearing and seal 26. Because these screw conveyors are tied to the disk impeller motion and the disk impellers have opposite rotation 8 and 9, the screw conveyors in this design have an opposite slope in order to make a consistent movement of material upward in both cases. A base support 27 anchors the assembly.

On the periphery of the disks is a prime mover 28 to turn the disk impellers in counter-rotation. This prime mover 28 can be a motor or another source of motive power such as wind or water power. The motor can be coupled to the hub or another part of the disk impellers in order to turn them. In this instance, the prime mover is coupled to a peripheral drive wheel 29 which simultaneously contacts the bottom disk impeller 6 at a bottom drive track 30, and the top disk impeller 7 at a top drive track 31. The rotation of the drive wheel 29 would therefore turn the two disk impellers in opposite directions. The drive wheel would preferably be a straight or spiral bevel gear, and the drive tracks would be compatible gear tracks. Support wheels such as at 32 contacting the opposite side of the disk impeller from the drive tracks will help to maintain a consistent engagement of the drive wheel 29 with the drive track such as at 30. Sleeper wheels such as at 33 also maintain a consistent separation of the disks, and are supported by sleeper wheel supports such as at 34.

Inboard of the drive wheels are barrier walls to shield the drive components from the products inside, and to direct their flow. The drive shield wall 35 is an annular wall attached to the top disk impeller, and is a backup barrier to prevent the products from the interior of the photobioreactor from clogging the drive system. Inboard of the drive shield wall 35 is the output deflector wall 36, which is also an annular wall, but this time attached to the bottom disk impeller, and angled inward so that the outward flow from the periphery is deflected downward to the heavy products exhaust port 13 and the heavy products collection trough 14. On the top of this output space, an output vent 37 allows remaining gases from the heavy product to escape. The collection trough 14 for the heavy product can contain a conveyor to further collect it, such as an annular heavy product screw conveyor 38 in the bottom of the trough, ending in a tangential branch for dumping the product into a hopper.

Inboard of these barrier walls, the separation of the disks narrows to the pinch section 39, where heavy output products are squeezed and concentrated, beginning with the pinch opening 40, where the workspace narrows.

The passage of feed into the workspace, while the disk impellers are in motion, creates a fractal network of vortices in the shear layer, with lighter products converging in a sink flow 17 into the axial exhaust port 18. At the same time, radiant energy, selected from the range of wavelengths from infrared to ultraviolet, is transmitted by a radiant energy source 41, so that it is absorbed into the feed 42 in the workspace.

This radiant energy transmission is done by making the disk impellers transparent or conductive to the radiant energy. For this example of an algae photobioreactor, the transparent disks allow the energy from sunlight or other artificial light energy to pass through them into the feed to be absorbed, including the wavelengths most beneficial for algae growth.

If the algae can benefit from the maximum amount of exposure to light, it is preferable for both disk impellers 6 and 7 to be transparent, and for there to be a light source both above and below the disks. This can be done with a reflector for a single light source such as the sun, or with duplicate artificial light sources above and below the disks. If the photobioreactor described here is duplicated in a stack, then the light source for the bottom of one photobioreactor can serve as the light source for the top of another. As an alternative, a single light source can be reflected back into the feed from a mirror finish on the disk impeller opposite the transparent disk impeller.

As the disk impellers slowly turn, the algae in the workspace are slowly swirled and rotated in the vortex flows, being exposed to light from every side, and continuously absorbing energy, like a roast being rotated on a spit. Heat flux due to forced convection sweeping the heat transfer surfaces is 50 W/cm2 which is better than static heating (pool boiling) at only 20. Controlled agitation of the algae maximizes the energy flux into them. This controlled agitation also provides radially inward pathways for the extraction of oxygen from photosynthesis, ammonia, H2S, oil, and clean water through the axial exhaust port 18, here shown as an opening at the center of the top disk. The axial extraction of light fractions enables a continuous process which favors photosynthesis by extracting the products.

The disk impellers may be solid transparent disks, screens, radial arms, or other configurations and materials permitting flux of radiant energy into the workspace. Ultraviolet radiant energy can thus have enhanced disinfecting by churning the feed so that microbes are exposed and killed by UV because suspended solids offer them no effective shade.

Figure 2:
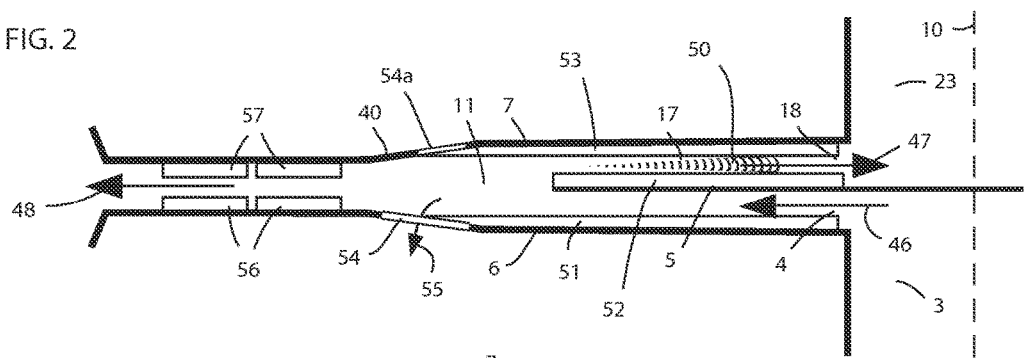
FIG. 2 shows a close-up of a portion of the reactor shown in FIG. 1, with more detail for the workspace.

FIG. 2 shows a close-up of the left side of the workspace 11 in FIG. 1. The feed flow into the photobioreactor is shown at 46, and the sink flow for light products to axial extraction out of the photobioreactor is shown at 47, as well as the peripheral flow outward for heavy products 48. The feed in the axial feed conduit 3 comes through the axial feed port 4 and enters the photobioreactor in the space underneath the baffle 5, which is located between the bottom disk impeller 6 and the top disk impeller 7. The feed flow is enhanced by vanes attached to the impellers, such as those shown in FIGS. 7-15. The vanes on the bottom impeller are indicated by 51, the vanes on the baffle are at 52, and the vanes on the upper impeller are shown at 53. In this example, the baffle is assumed to be attached to the bottom disk impeller so they co-rotate, so the vane pattern of the vanes on the top of the baffle 52 will resemble the vanes on the bottom impeller 51.

An optional crossflow filter 54 inset into the bottom disk impeller can be used to remove fluid from a sludge in a fluid flow 55, by making use of the force produced when the sludge is forced outward by centrifugal force while being squeezed by the pinch section 40 where the disks impellers have a narrower separation. The crossflow filter is a sintered metal or plastic screen, made flush to the interior surface of the disk impeller facing the workspace, and usually backed by a watertight plug to close it when it is not in use. This crossflow filter would be used for dewatering an algae sludge, with the disk impellers spinning much faster than they normally would for general algae growth. This faster rotation would tend to spin all of the algae outward from the workspace, to clear the way for a fresh batch. The dewatered algae sludge concentrate would then proceed outward into the pinch section 40.

A similar perforated opening gas vent 56a in the top disk impeller could be used to vent gases that would tend to accumulate in bubbles on its interior surface, and be swept out toward the periphery by the vanes. There would be a smaller net area of opening needed for the vent in this case. The vented gases should be monitored as to their composition, as part of the sensors which would monitor the condition of the feed in the workspace, measuring factors such as temperature, pH, density, nutrients and mass flow.

Optional rugose ridges, such as 56 on the bottom impeller and 57 on the top impeller, can interrupt and constrict the outward flow 48 flow still further, causing pressure waves for osmotic shock at low speed or cavitation in fluids at high speed, as another way to transform the feed. These rugose ridges are described more fully in the discussion of FIG. 5.

Figure 3:
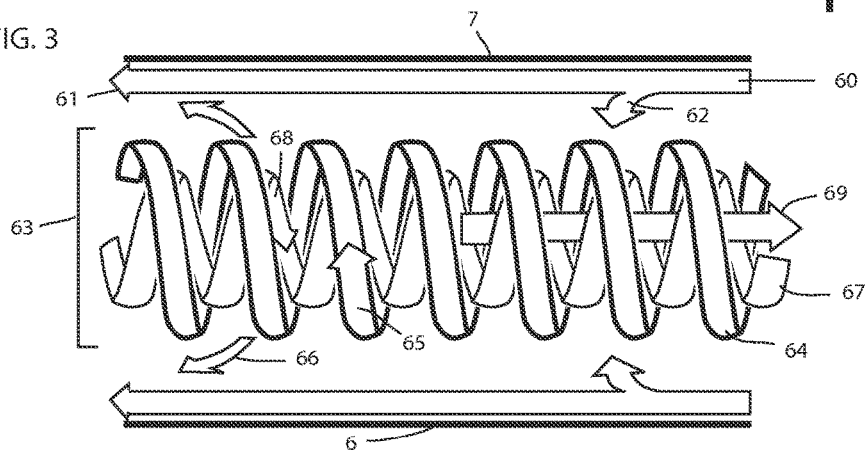
FIG. 3 shows a schematic side view of the flow patterns in the workspace.

FIG. 3 shows a cross section close-up of the flows in the workspace. Next to each disk impeller 6 and 7 is a boundary layer 60, characterized by a laminar flow 61 of the feed, some of which flows inward 62 to the shear layer 63, which is located between the boundary layers. The shear layer contains a branching area-preserving network of vortices, with larger vortices toward the axis collecting the products of smaller vortices toward the periphery. The outer region of a typical vortex is shown at 64, with its flow at 65. Heavier products are spun out by amplified centrifugal force in the photobioreactor and migrate outward, first to the outer regions of the vortex and then to the boundary layer in an outward flow 66. Meanwhile, the inner part of the vortex 67 has a flow 68 that collects the lighter parts, which are drawn inward toward the axis of rotation in a sink flow 69.

In the case of algae, under normal growth conditions the boundary layers would comprise mostly a water, $CO_2$ and nutrient feed, and the algae would concentrate in the vortices in the shear layer, where they would divide and grow.

Figure 4:
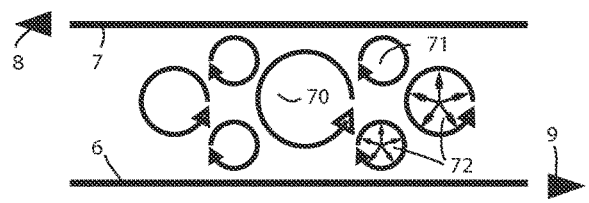
FIG. 4 shows a head-on view of the flow patterns in the workspace, featuring nested vortices.

FIG. 4 shows an orthogonal cross section of the workspace, with a flow pattern of vortices, where the clockwise flow of a larger vortex 70 may be surrounded by counter-clockwise flows 71 in the overall turbulence pattern. Both of these types of vortices contribute to the overall sink flow network by creating centrifugal separation 72 of the feed. For algae, the rotations of the algae in these vortices would expose all of them more completely to the light coming through the disk impellers, while at the same time the centrifugal separation 72 would strip out the products with a lower specific gravity, such as extruded lipids, into the sink flow. Recent work by VG Energy has shown how the lipid trigger can be manipulated to make algae overproduce and extrude lipids, instead of storing them in their bodies. If these extruded lipids can be continuously stripped away from the algae, they will not contaminate the environment of the algae and inhibit their growth. The live algae are typically kept apart by electrical repulsion, and kept buoyant by their motility as well as internal gas vacuoles or gas bubbles on their membranes, but as they die they would become less buoyant and would migrate into the heavier products flow outward. Thus, the dead algae would tend to collect on the periphery of the reactor, and the lighter products such as lipids would be continuously collected in the axial sink flow.

If the goal of the photobioreactor is the mass production of algae, then the excess algae be extruded at the periphery, leaving a constantly growing and dividing stock in the workspace. This separation could be assisted by the clumping of algae by autoflocculation. As the algae consume the carbon dioxide being introduced axially, the outer regions of the workspace grow to have a higher pH, which, together with flocculants in the solution such as calcium carbonates and calcium phosphates, cause the algae to clump together. This increases the centrifugal force on the clumps, and causes them to spin outward to the periphery. Using ports in the disk impellers for introducing flocculant chemicals directly into the solution at a given radial distance from the axis of rotation 10 can allow more precise control of this process.

Figure 5:
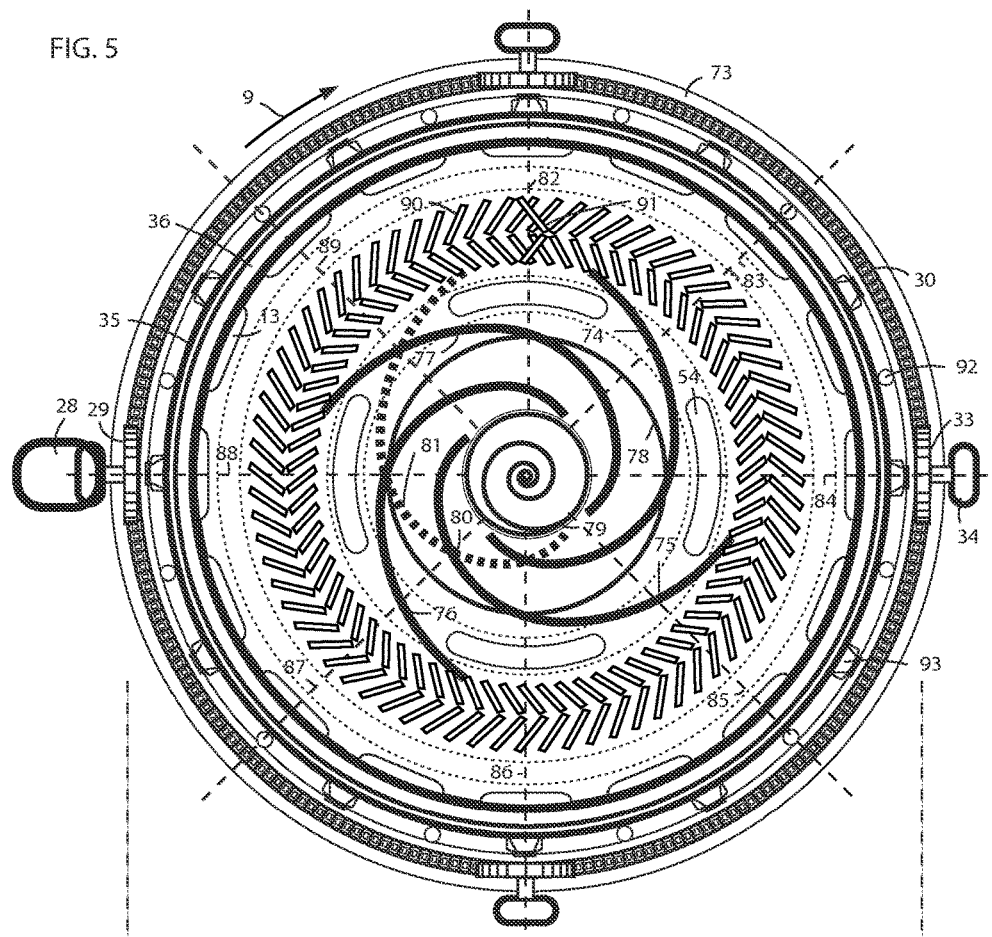
FIG. 5 shows a top view of the bottom disk impeller, showing the ports, vanes and other components.

In FIG. 5 is a top view of the bottom impeller 73, which has a clockwise rotation 9. It can be made of any suitable material, such as plastic, glass, ceramic, metal or any practical material. In the case of transparent disk impellers for algae, the material used should not block the most beneficial wavelengths. There are, in this example, four vanes 74, 75, 76 and 77, attached to the impeller and made of a suitable material, shaped in this case according to a spiral. The edge of the baffle 5 is indicated at 78. In the center, at the axis of rotation, is the apex of the screw feed conveyor 79, which preferably should be conical to produce a more lateral feed underneath the baffle.

The vanes form crossing intersections such as 80 with the corresponding but inverted vanes on the underside of top impeller, such as 81, which is here seen as if looking down through the top impeller at a moment when the vanes are crossing. These moving intersections form a rhythmical flow along eight well-defined intersection axes: 82, 83, 84, 85, 86, 87, 88 and 89. This rhythmical flow is shown in FIGS. 7-15. The mass flow along these eight axes is the basis for the organized turbulence of the flow of the shear layer between the disks. This mass flow through the boundary layers also prevents the formation of biofilm which can coat the disk impellers and block light. The vanes push the feed outward as the disk impellers turn, and the intersection points moving outward along the intersection axes form moving zones of increased shear and vorticity which reinforce the sink flow moving inward toward the axis of rotation.

A pattern of rugose ridges 90 can be part of the peripheral section, as also seen in FIG. 2. They are designed to intersect the corresponding rugose ridges from the top impeller, such as shown by a sample at 91. These rugose ridges are for causing osmotic pressure waves at low speeds or cavitation in liquids at high speeds, or to aid in the comminution of a more solid feed. In the case of algae, the rugose ridges would produce osmotic shock, and, at high speed, cavitation bubbles in the water, which would explode the algae cell membranes and release the contents, allowing a better interaction with digestive enzymes for more complete recovery of any stored lipids.

The output deflector wall is shown at 36. This barrier, which can be made part of the impeller or separately attached, deflects the processed heavy products downward into the heavy products outlets 13, which are here shown partially covered because of the overhang of the output deflector wall 36. The drive shield wall is shown at 35. This wall is actually attached to the top disk impeller, but is added here for clarity. A gas vent 92 and a drive shield wall brace 93 are also shown. The drive shield wall brace 93 aids in the attachment of the drive shield wall to the top disk impeller. If a similar brace and attachment is also built into the disk impeller for the output deflector wall 36, then the disk impeller design can be made to be interchangeable; usable for either the top or the bottom disk impeller.

The optional annular crossflow filter inset into the bottom disk impeller is shown at 54, which can be used to remove fluid from a sludge as discussed and shown in cross section in FIG. 2. A fuller description of this annular crossflow filter in a radial counterflow reactor can be found in the applicant's U.S. Pat. No. 7,757,866 entitled "Rotary Annular Crossflow Filter, Degasser and Sludge Thickener."

At the periphery of the disk, a drive track 30 engages the gear teeth of the drive wheel 29 which is driven by a motor 28, or a sleeper wheel such as 33 which has a sleeper wheel support 34. The drive can be a gear drive, a belt drive, a chain drive, or a friction drive, as needed for the application requirements, including noise, speed, and torque.

Figure 6:
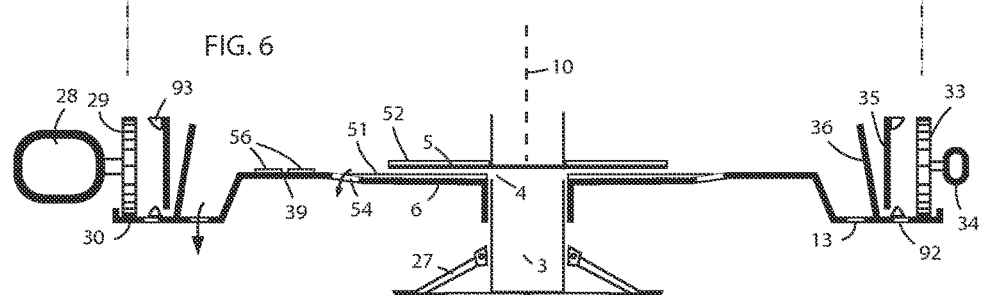
FIG. 6 shows a side cross section view of the bottom disk impeller shown in FIG. 5.
Figure 7:
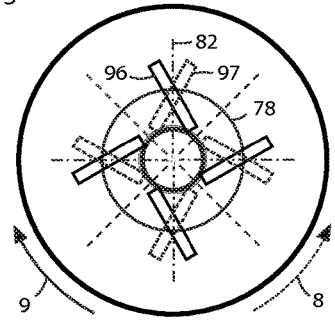
FIG. 7 shows the superimposed patterns of the vanes for the top and bottom impellers, at a starting point in their counter-rotation.
Figure 8:
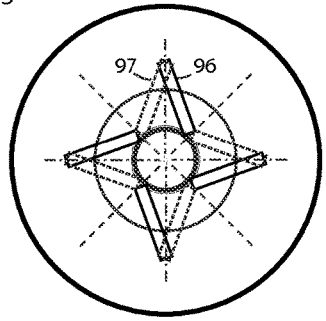
FIG. 8 shows the superimposed patterns of the vanes for the top and bottom impellers, rotated by 10° in opposite directions.
Figure 9:
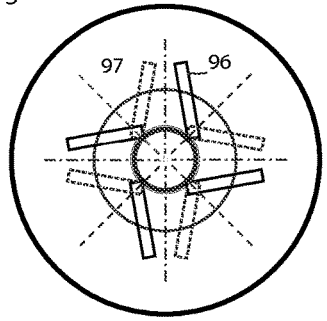
FIG. 9 shows the superimposed patterns of the vanes for the top and bottom impellers, rotated by 20° in opposite directions.
Figure 10:
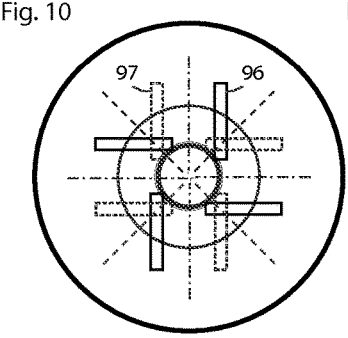
FIG. 10 shows the superimposed patterns of the vanes for the top and bottom impellers, rotated by 30° in opposite directions.
Figure 11:
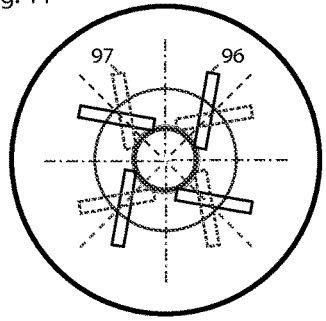
FIG. 11 shows the superimposed patterns of the vanes for the top and bottom impellers, rotated by 40° in opposite directions.
Figure 12:
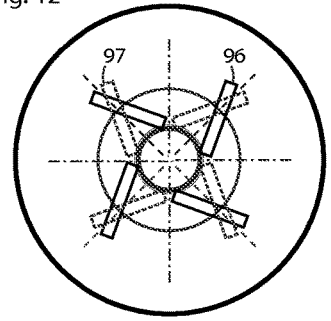
FIG. 12 shows the superimposed patterns of the vanes for the top and bottom impellers, rotated by 50° in opposite directions.
Figure 13:
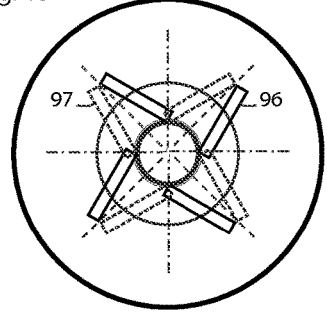
FIG. 13 shows the superimposed patterns of the vanes for the top and bottom impellers, rotated by 60° in opposite directions.
Figure 14:
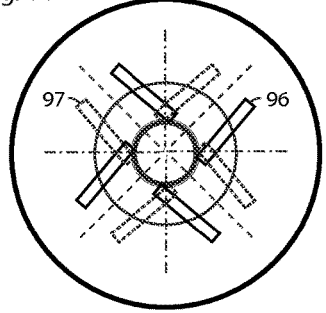
FIG. 14 shows the superimposed patterns of the vanes for the top and bottom impellers, rotated by 70° in opposite directions.
Figure 15:
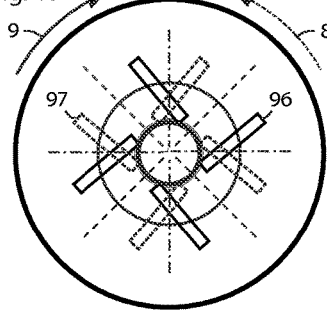
FIG. 15 shows the superimposed patterns of the vanes for the top and bottom impellers, rotated by 80° in opposite directions.

FIG. 6 shows a side view cross section of the bottom disk impeller 73 of FIG. 5, drawn to the same scale, as also shown in FIG. 1. The bottom disk impeller 6 has an axial feed conduit 3 and an axial feed port 4 where the feed enters underneath the baffle 5. A motor 28 drives a drive wheel 29 which engages a drive track 30 to rotate the disk impeller 6 around the axis of rotation 10, stabilized by sleeper wheels such as 33 and other supports such as sleeper wheel support 34 and a base support 27. The heavy products exhaust port is shown at 13. The disk impeller vanes 51 and the baffle vanes 52 as well as the crossflow filter 54 are also shown in FIG. 2. In the peripheral pinch section b are the rugose ridges 56. Further toward the periphery are the output deflector wall 36 and the drive shield wall 35 with optional gas vents 92. A drive shield wall brace 93 can be built into a generic disk impeller design to enable attachment of the disk shield wall to the top disk impeller.

FIGS. 7-15 show the successive rotation positions of a set of four straight vanes on two counter-rotating disk impellers. Each figure represents a rotation of 10°, so they make a repeating cycle of 90°. The direction of rotation for the top disk impeller is at 8, and the direction of rotation for the bottom disk impeller is shown at 9. The location of the edge of the baffle is at 78. A straight vane on the bottom disk impeller is shown at 96, and a straight vane on the top disk impeller is at 97. The successive positions for these vanes are shown in each figure, and the parts representative of the top disk impeller are shown with dashed lines. The intersection points of the vanes form eight radial axes, such as at 82, which are the organizing axes for the sink flow.

Liquid Impellers

Figure 18:
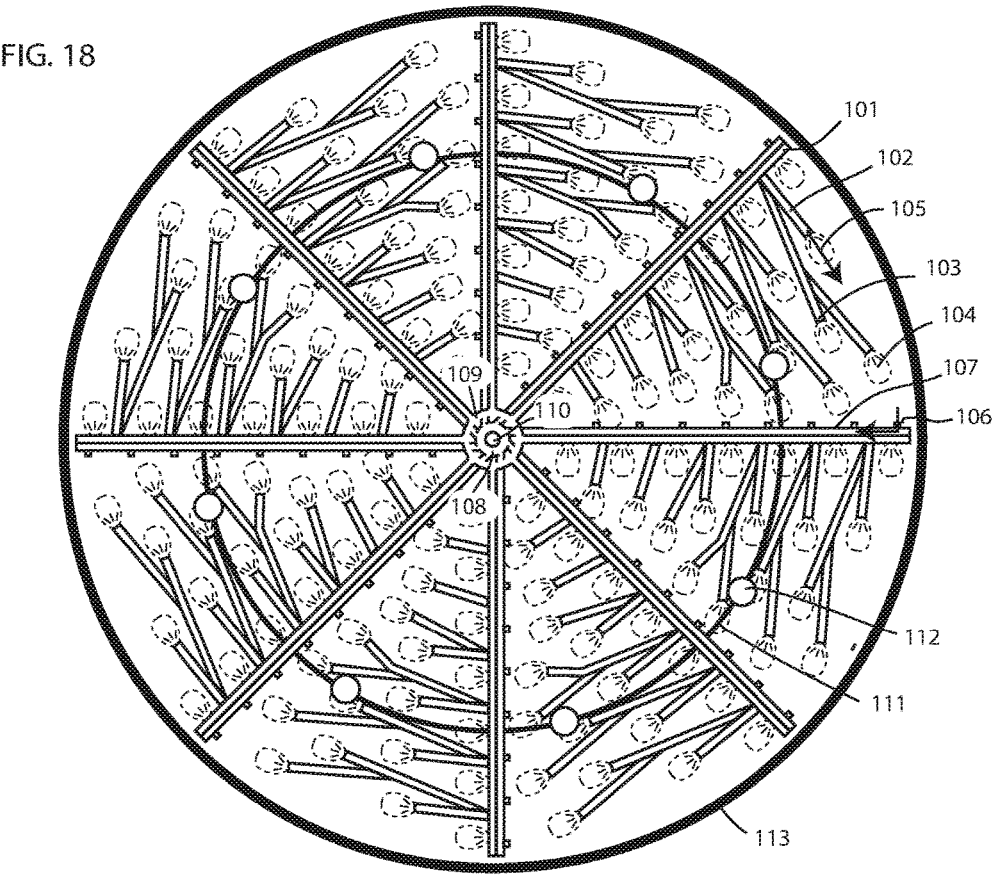
FIG. 18 shows a top view of an array of jets to create a moving liquid disk impeller.
Figure 19:
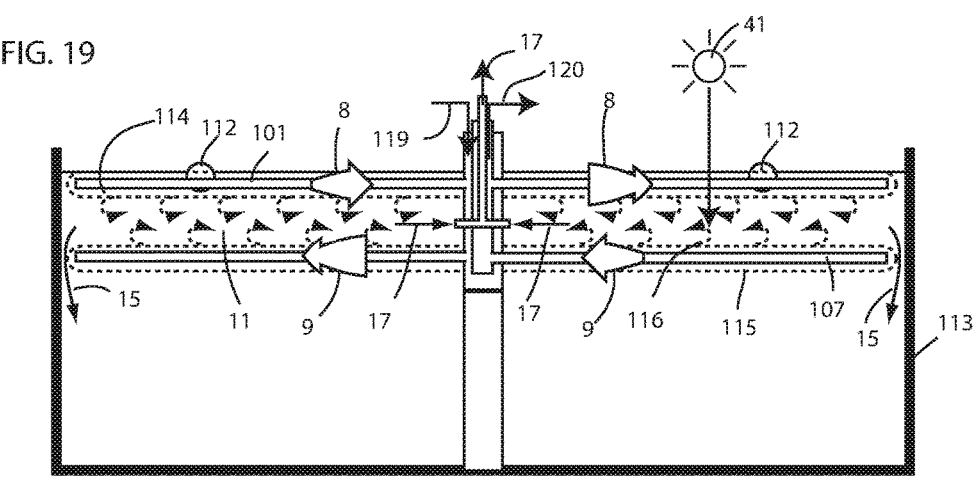
FIG. 19 shows a cross section of two liquid impellers in a photobioreactor for aquaculture.

FIGS. 18-19 show another example of a photobioreactor, featuring liquid impellers, which is especially useful for aquaculture and for UV disinfection. FIG. 18 shows a top view of an array of jets to create a moving liquid disk impeller. Preferably this array is static, and only the liquid moves. The liquid is fed through a network of supply pipes. An example of a main supply pipe is shown at 101, and 102 shows a branch supply pipe. An example of a liquid jet nozzle is at 103. When liquid such as water is forced through this nozzle, it makes a jet area of water pressure 104 which, in combination with the flow from the other jets, creates an overall direction of flow 105 for the liquid layer, forming a liquid impeller disk. Preferably the jets should be in a planar arrangement, parallel to the surface of the water, and the jet nozzles are configured to spray a pattern which spreads more horizontally than vertically, to fill in the liquid impeller layer more completely and to keep it from becoming too thick.

In addition to the supply pipes spraying into the liquid impellers, preferably there are also drain pipes. Drain inlets 106 feed into drain pipes 107 which lead back to a central drain 108, which is distinct from the central supply pipe 109. An axial exhaust pipe 110 takes out the sink flow products from the workspace. Support frame members 111 keep the pipes and jets from becoming distorted or out of place, and support floats 112 can relieve their weight. A peripheral wall 113 sets a boundary for the photobioreactor.

FIG. 19 shows a cross section of two liquid impellers in the photobioreactor. The top liquid impeller 114 is created by jets from fluid such as water carried by main supply pipes such as at 101, fed by a central supply flow 119, creating an overall direction of flow 8. In this case the upper boundary of the upper impeller is equal to the surface of the water. The bottom liquid impeller 115 is created by a similar array of pipes and jets, but pointing in the opposite direction, so as to produce an opposite direction of rotation 9 in the liquid impeller. Oppositely flowing turbulence 116 extending from the boundary layer into the shear layer in the workspace 11 creates a vortex network, with a sink flow of lighter products 17 being drawn into the central exhaust, while a flow of heavier products 15 flows from the periphery. A network of drain pipes 107 is preferably also present, leading into a central drain outlet 120. A support float 112 helps manage the weight of the pipes, and the peripheral wall is shown at 113. The liquid impellers can be used within a cylindrical tank or in a pond or lake which is larger than the width of the array of jets. One liquid impeller can also be used by itself at some distance below the surface, allowing the surface of the water and the liquid impeller to define the workspace.

Radiant energy 41 is applied in this case by sunlight shining through the transparent water to encourage growth in the workspace. The liquid impellers can introduce nutrients such as food and beneficial gases into the workspace, by first dissolving these components into the water carried in through the supply pipes. The drain pipes can help draw out any waste products that find their way into the liquid impeller layer. The liquid impellers can also help regulate temperature in the workspace. For example, on a hot day, the upper impeller layer can be supplied with colder water, which will diffuse downward and cool the workspace.

Aquaculture can include the cultivation of many different types of organisms, such as algae, shrimp, fish, oysters, and seaweed, either alone or in combination. The younger or weaker organisms would be more likely to be passively carried by the vortices created in the workspace, but the larger or stronger mobile organisms would be able to be actively able to swim into the disk impellers themselves, where they could have more direct access to food in the liquid impeller layer, with less competition than in the workspace. This self-separation of organisms could aid in the harvesting of the more mature individuals.

Biochar Processor

Another example of a radial counterflow reactor with applied radiant energy is used for the processing of biomass for biochar, bio-oil, and combustible gas. In this case the feed 1 is different, but the general design of FIG. 1 is the same, with the applied energy 41 absorbed into the feed 42 in the workspace 11 being infrared or heat energy heating the disk impellers 6, 7, which are made of a refractory material that can resist heat, pressure and wear. The heating can be done by external means, such as flames heating a portion of the disk impeller as it passes, or internal means, such as heating coils built into the rotating disk impellers. The combustible gas output of the process can be burned to help supply this heat.

A wide variety of cellulosic biomass feed stocks can be used, including wood chips, sawdust, switchgrass, bagasse, corn stover, plant cuttings, seaweed, and algae cake, and other biodegradable waste. The feed should be ground before it is input into the bioreactor to enable it to be churned by the turbulence in the workspace, and dried to reduce the energy needed to convert it.

The biomass feedstock is churned and heated in the workspace 11 of the radial counterflow reactor, where it undergoes thermal decomposition in an oxygen-starved environment, forming biochar and gaseous products that comprise bio-oil and syngas. The pyrolysis of triglycerides and other organic compounds in the feedstock forms carboxylic acids, alkans, alkenes, aromatics, and other volatile compounds that can be condensed into bio-oil. Syngas is comprised of hydrogen and carbon monoxide. In addition, there will be steam and other gaseous. The biochar may contain potash and other compounds, depending on the feed. More applied energy 41 applied to the bioreactor for higher temperatures will create more gasification and less char. The infrared energy can come from heated disk impellers, or heated sand mixed with the feed, such as is used by BTG-BTL in their design for a rotating cone reactor. The pyrolysis can be fast pyrolysis, for a higher proportion of bio-oil output, or slow pyrolysis, for more biochar out. The present design for a bioreactor will be more efficient in the processing because of the high turbulence and rapid stripping of the light products from the feed.

In the workspace 11, the pyrolysis of triglycerides and other organic compounds in the feedstock forms carboxylic acids, alkans, alkenes, aromatics, and other volatile compounds, which comprise the light products stream 99. Producer gas, a more complete gasification product created by even more heat and pressure, is comprised of carbon monoxide, steam, hydrogen and other compounds, and is useful for producing fuel and chemicals. The biochar product is useful for soil remediation and carbon sequestration, and also can be burned as a fuel.

Figure 16:
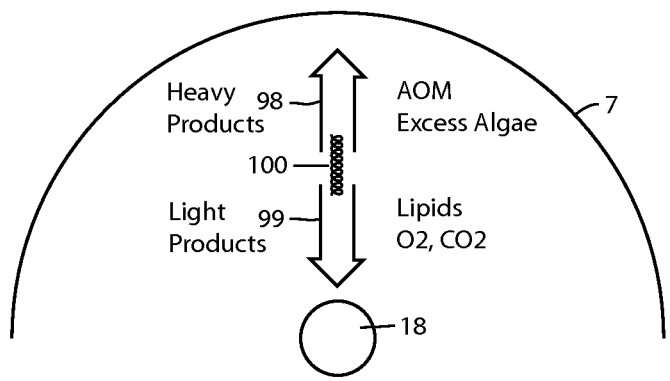
FIG. 16 shows a set of flows for a radial counterflow algae photobioreactor.
Figure 17:
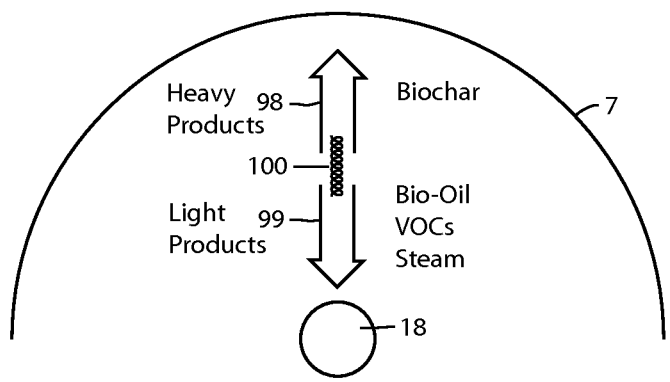
FIG. 17 shows a set of flows for a radial counterflow biochar bioreactor.

FIGS. 16 and 17 shows examples of sets of flows for a radial counterflow reactor, showing the outline of a disk impeller 7, the axial exhaust port 18, the heavy products flow 98 toward the periphery, and the inward light products sink flow 99, as separated by a vortex network 100. In FIG. 16, for a radial counterflow algae photobioreactor, the heavy products flow 98 comprises heavy products with more specific gravity than water in the feed, such as algogenic organic matter (AOM), senescent algae, and flocculated algae. The light flows would be the components with less specific gravity, such as gases, including oxygen and excess $CO_2$ and extruded lipids. Increasing the rotation speed of the disk impellers as well as the suction at the axial exhaust port 18 would increase the radial counterflow separation effects, to make healthy excess algae that is crowding the workspace also move outward. When the central suction is decreased and the rotation speed is increased, the net effect is to clear out the workspace, for cleaning or restocking. In FIG. 17, the heavy products for a biochar reactor would include biochar, and the light products would include bio-oil, volatile organic compounds (VOCs) and steam.

The radial counterflow reactor with applied radiant energy of this disclosure has here been described for its use as an algae churn, in aquaculture and as a biochar oven. However, it will be appreciated by those skilled in the art that a continuous separator of this type, making use of applied energy to transform the feed while simultaneously separating the byproducts, can find use in other applications, such as chemical engineering, refining, and food processing.

For example, radiant energy in radial counterflow can aid in drying, cleaning or processing solids while simultaneously extracting vapors and gases, or other continuous processing with centrifugal force and heating. It can also be of use in classifying, separating and assorting solids with heat treatment, or with separating or classifying gases and liquids by induced swirl and rotational hydrodynamic extraction. The radial counterflow reactor with applied radiant energy is also of use as a pump where one fluid is pumped by contact or entrainment with another within a rotary impeller, or by using one or more jets.

While the embodiments of the present invention have been particularly shown and described above, it will be understood by one of ordinary skill in the art that various changes in form and details may be made therein without departing from the spirit and scope of the present invention as defined by the following claims.

The applicants claim:

1. A radial counterflow apparatus with radiant energy applied to the transformation of a feed, comprising:
   a source of radiant energy in a wavelength from infrared to ultraviolet;
   two counter-rotatable disk impellers with a common axis of rotation, defining a workspace between them, the disk impellers being at least one of optically transparent or thermally conductive to the radiant energy, at least one impeller having an output deflector wall;
   a baffle disposed between said two coaxial counter-rotatable disk impellers;
   an axial feed port approximately centered on said axis of rotation, disposed underneath the baffle, and communicating with the workspace;
   a feed transport communicating with the axial feed port;
   a heavy products exhaust port located on the periphery of the workspace to receive heavy products including any heavy products deflected from the deflector wall;
   an axial exhaust port approximately centered on said axis of rotation, disposed above the baffle, and communicating with the workspace;
   an axial suction pump communicating with the axial exhaust port;
   a drive wheel to cause counter-rotation connected to the disk impellers, and a feed.

2. The apparatus of claim 1, wherein the radiant energy comprises visible light, and at least one of said disk impellers comprise a transparent portion adjacent the workspace.

3. The apparatus of claim 1, wherein the source of radiant energy comprises an infrared source embedded in at least one of said disk impellers being conductive to the radiant energy.

4. The apparatus of claim 1, wherein said disk impellers narrow in separation toward the periphery of the workspace.

5. The apparatus of claim 1, wherein said disk impellers comprise vanes extending into the workspace, the vanes of the disk impellers being disposed in opposition across the workspace.

6. The apparatus of claim 1, wherein said disk impellers comprise rugose ridges, the rugose ridges of the disk impellers being disposed in opposition across the workspace.

7. The apparatus of claim 1, wherein at least one of said disk impellers comprises an annular crossflow filter.

8. The apparatus of claim 1, wherein said baffle comprises vanes extending into the workspace.

9. The apparatus of claim 1 wherein the peripheral drive wheel contacts both of the two counter-rotatable disk impellers.

10. The apparatus of claim 1, wherein the feed comprises algae, water, carbon dioxide and nutrients.

11. The apparatus of claim 10, wherein lipids are extracted through the axial exhaust port by the axial suction pump.

12. The apparatus of claim 1, wherein the drive wheel comprises a straight bevel gear.

13. The apparatus of claim 1, wherein the drive wheel comprises a spiral bevel gear.

14. The apparatus of claim 1, further comprising a drive track to connect to the drive wheel.

15. The apparatus of claim 1, further comprising sleeper wheels.

* * * * *